(12) United States Patent
Fritzler

(10) Patent No.: US 7,452,676 B2
(45) Date of Patent: Nov. 18, 2008

(54) MONOCLONAL ANTIBODIES TO RNA BINDING PROTEIN GW182

(75) Inventor: Marvin J. Fritzler, Calgary (CA)

(73) Assignee: UTI Limited Partnership, Calgary (CA)

( * ) Notice: Subject to any disclaimer, the term of this patent is extended or adjusted under 35 U.S.C. 154(b) by 0 days.

(21) Appl. No.: 10/541,938

(22) PCT Filed: Jan. 16, 2004

(86) PCT No.: PCT/IB2004/000100

§ 371 (c)(1),
(2), (4) Date: May 15, 2006

(87) PCT Pub. No.: WO2004/062462

PCT Pub. Date: Jul. 29, 2004

(65) Prior Publication Data

US 2006/0264617 A1  Nov. 23, 2006

Related U.S. Application Data

(60) Provisional application No. 60/440,326, filed on Jan. 16, 2003.

(51) Int. Cl.
*G01N 33/533* (2006.01)

(52) U.S. Cl. .................. 435/7.1; 436/547; 436/548; 530/386; 530/387.1; 530/388.1

(58) Field of Classification Search .................. 530/386, 530/387.1, 388.1; 435/7.1; 436/547, 548
See application file for complete search history.

(56) References Cited

OTHER PUBLICATIONS

Campbell, Ailsa. Immunoassay. Edited by Diamandis et al. 1996. pp. 95-115.*
Eystathioy et al., Molecular Biology of the Cell. vol. 13, 1338-1351. Apr. 2002.*
Eystathioy et al., Hybridoma and Hybridomics. Apr. 2003. vol. 22, No. 2, pp. 79-86.*
Kohler, Geroges. Science. Sep. 1986. 233(4770):1281-1286.*

* cited by examiner

*Primary Examiner*—Bao-Thuy L Nguyen
(74) *Attorney, Agent, or Firm*—Fulbright & Jaworski

(57) ABSTRACT

The present invention includes antibodies to human GW182 protein and the use of those antibodies in clinical and diagnostic assays.

8 Claims, 2 Drawing Sheets

Figure 1

| Position number | Sequence | Position | 2D6 (IgM) | 4B6 (IgG$_1$) | 5C6 (IgG$_{2a}$) | 6D7 (IgG$_1$) |
|---|---|---|---|---|---|---|
| 6 | EKDGLRNSTGLGSQN | 26–40 | | | | |
| 7 | RNSTGLGSQNKFVVG | 31–45 | | | | |
| 29 | QCSTIGQMPNNQSIN | 141–155 | | | | |
| 30 | GQMPNNQSINSKVSG | 146–160 | | | | |
| 36 | SEVSGTQKVSFSGQP | 176–190 | | | | |
| 37 | TQKVSFSGQPQNITT | 181–195 | | | | |
| 77 | GKTFTNGWKSTEEED | 381–395 | | | | ■ |
| 87 | EKGTGESQSRDRRKI | 431–445 | | | | |
| 88 | ESQSRDRRKIDQHTL | 436–450 | | | | |
| 92 | NRTDLDPRVLSNSGW | 456–470 | | | | |
| 93 | DPRVLSNSGWGQTPI | 461–475 | | | | |
| 105 | GNDTSSVSGWGDPKP | 521–535 | | | | |
| 106 | SVSGWGDPKPALRWG | 526–540 | | | | |
| 109 | DSKGSNCQGGWEDDS | 541–555 | | | | |
| 117 | KNKQGWGDGQKSSQG | 581–595 | | | | |
| 118 | WGDGQKSSQGWSVSA | 586–600 | ■ | | ■ | |
| 119 | KSSQGWSVSASDNWG | 591–605 | ■ | | ■ | |
| 125 | SSGGSDSDRSVSGWN | 621–635 | | ■ | | |
| 126 | DSDRSVSGWNELGKT | 626–640 | ■ | ■ | ■ | |
| 127 | VSGWNELGKTSSFTW | 631–645 | ■ | | | |
| 130 | GNNINPNNSSGWDES | 646–660 | | | | ■ |
| 133 | SKPTPSQGWGDPPKS | 661–675 | | | | |
| 134 | SQGWGDPPKSNQSLG | 666–680 | | | | |
| 135 | DPPKSNQSLGWGDSS | 671–685 | | | | |
| 136 | NQSLGWGDSSKPVSS | 676–690 | | | | |
| 137 | WGDSSKPVSSPDWNK | 681–695 | | | | |
| 138 | KPVSSPDWNKQQDIV | 686–700 | | | | |
| 139 | PDWNKQQDIVGSWGI | 691–705 | | | | |
| 146 | AKEEEPTGWEEPSPE | 726–740 | | | | ■ |
| 150 | MEIDDGTSAWGDPSK | 746–760 | | | | |
| 154 | VNMWNKNVPNGNSRS | 766–780 | | | | |
| 159 | TPASAISNKEASSGS | 791–805 | | | | ■ |
| 160 | ISNKEASSGSGWGEP | 796–810 | | | | ■ |
| 161 | ASSGSGWGEPWGEPS | 801–815 | | | | ■ |
| 162 | GWGEPWGEPSTPATT | 806–820 | ■ | | | |
| 176 | DDMPLPGNRPTGWEE | 876–890 | | | | ■ |
| 177 | PGNRPTGWEEEEDVE | 881–895 | | | | ■ |
| 178 | TGWEEEEDVEIGNWN | 886–900 | | | | ■ |
| 185 | SSKGLSGKKRRRERG | 921–935 | | | | |
| 187 | RRERGMMKGGNKQEE | 931–945 | | | | |
| 191 | FVKQFSNISFSRDSP | 951–965 | | | | |
| 192 | SNISFSRDSPEENVQ | 956–970 | | | | |
| 198 | MEIDKHSLNIGDYNR | 986–1000 | | | | |
| 199 | HSLNIGDYNRTVGKG | 991–1005 | | | | |
| 200 | FGYNRTVGKGPGSRP | 996–1010 | | | | |
| 201 | TVGKGPGSRPQISKE | 1001–1015 | | | | |
| 202 | PGSRPQISKESSMER | 1006–1020 | | | | ■ |
| 203 | QISKESSMERNPYFD | 1011–1025 | | | | |
| 221 | PLSSSQPNLRAQVPP | 1101–1115 | | | | |
| 226 | LLKYAPNNGGLNPLF | 1126–1140 | ■ | | | |
| 227 | PNNGGLNPLFGPQQV | 1131–1145 | ■ | | | |
| 228 | LNPLFGPQQVAMLNQ | 1136–1150 | | | | |
| 233 | SQLQRLLAQQQRAQS | 1161–1175 | | | | |
| 234 | LLAQQQRAQSQRSVP | 1166–1180 | | | | |
| 235 | QRAQSQRSVPSGNRP | 1171–1185 | | | | |
| 239 | GRPLSVQQQMMQQSR | 1191–1205 | | | | |
| 270 | SPNGSSSVNWPPEFR | 1346–1360 | ■ | | | |
| 271 | SSVNWPPEFRPGEPW | 1351–1365 | | | | |
| 274 | KGYPNIDPETDPYVT | 1366–1380 | | | | ■ |
| 276 | KPYVTPGSVINNLSI | 1376–1390 | | | | |
| 287 | PLSSTAQSTSARNSD | 1431–1445 | | | | |
| 288 | AQSTSARNSDSKLTW | 1436–1450 | | | | |
| 298 | GQKPPLSTWDNSPLR | 1486–1500 | | | | |
| 299 | LSTWDNSPLRIGGGW | 1491–1505 | ■ | | | |
| 304 | SSWGESSSGRITNWL | 1516–1530 | ■ | | | |
| 319 | TTILAEFASEEEISR | 1591–1605 | | | | ■ |
| 320 | EFASEEEISRFFAQS | 1596–1610 | | | | ■ |
| 323 | QSLTPSPGWQSLGSS | 1611–1625 | | | | |
| 324 | SPGWQSLGSSQSRLG | 1616–1630 | | | | |
| 336 | WGPPSSSDPRGISSP | 1676–1690 | ■ | | | |
| 339 | SPINAFLSVDHLGGG | 1691–1705 | | | | |
| 340 | AFLSVDHLGGGGESM | 1696–1710 | | | | |

Figure 2

| Number | Sequence | Position | #1 | #3 | #10 |
|---|---|---|---|---|---|
| 6 | EKDGLRNSTGLGSQN | 26-40 | ■ | | |
| 7 | RNSTGLGSQNKFVVG | 31-45 | ■ | | |
| 18 | NNRMNAWGTVSSSSN | 86-100 | | | ▨ |
| 22 | STLNSASNHGAWPVL | 106-120 | | | ▨ |
| 29 | QCSTIGQMPNNQSIN | 141-155 | ▨ | | |
| 30 | GQMPNNQSINSKVSG | 146-160 | ▨ | | |
| 36 | SEVSGTQKVSFSGQP | 176-190 | | | |
| 37 | TQKVSFSGQPQNITT | 181-195 | ▨ | | |
| 45 | ELPSSNTGAWRVSTM | 221-235 | | | ▨ |
| 54 | GTTWGAYGSNYSGDK | 266-280 | | | |
| 55 | AYGSNYSGDKCSGPN | 271-285 | | | ▨ |
| 63 | QVNTNKGGGVWESGA | 311-325 | | | |
| 64 | KGGGVWESGAANSQS | 316-330 | | | |
| 65 | WESGAANSQSTSWGS | 321-335 | | | |
| 67 | TSWGSGNGANSGGSR | 331-345 | | ▨ | |
| 68 | GNGANSGGSRRGWGT | 336-350 | ▨ | | |
| 77 | GKTFTNGWKSTEEED | 381-395 | ■ | | |
| 78 | NGWKSTEEEDQGSAT | 386-400 | ■ | | |
| 87 | EKGTGESQSRDRRKI | 431-445 | | ▨ | |
| 88 | ESQSRDRRKIDQHTL | 436-450 | | ▨ | |
| 92 | NRTDLDPRVLSNSGW | 456-470 | | | |
| 93 | DPRVLSNSGWGQTPI | 461-475 | | ▨ | |
| 97 | WDTETSPRGERKTDN | 481-495 | ▨ | | |
| 105 | GNDTSSVSGWGDPKP | 521-535 | ■ | | |
| 106 | SVSGWGDPKPALRWG | 526-540 | ▨ | | |
| 117 | KNKQGWGDGQKSSQG | 581-595 | ■ | | |
| 118 | WGDGQKSSQGWSVSA | 586-600 | ■ | | |
| 133 | SKPTPSQGWGDPPKS | 661-675 | ■ | | |
| 134 | SQGWGDPPKSNQSLG | 666-680 | | | ■ |
| 135 | DPPKSNQSLGWGDSS | 671-685 | ▨ | | |
| 136 | NQSLGWGDSSKPVSS | 676-690 | | | |
| 137 | WGDSSKPVSSPDWNK | 681-695 | ■ | | ▨ |
| 138 | KPVSSPDWNKQQDIV | 686-700 | | | |
| 139 | PDWNKQQDIVGSWGI | 691-705 | | | |
| 148 | EPSPESIRRKMEIDD | 736-750 | | ▨ | |
| 150 | MEIDDGTSAWGDPSK | 746-760 | ■ | | |
| 154 | VNMWNKNVPNGNSRS | 766-780 | ▨ | ▨ | |
| 171 | WGSSSVGPQALSKSG | 851-865 | | ▨ | |
| 177 | PGNRPTGWEEEEDVE | 881-895 | | ▨ | |
| 185 | SSKGLSGKRRRERG | 921-935 | | ▨ | |
| 187 | RRERGMMKGGNKQEE | 931-945 | ■ | | |
| 189 | NKQEEAWINPFVKQF | 941-955 | | | ■ |
| 190 | AWINPFVKQFSNISF | 946-960 | | | |

| 191 | FVKQFSNISFSRDSP | 951-965 | | | ▨ |
|---|---|---|---|---|---|
| 192 | SNISFSRDSPEENVQ | 956-970 | | | ▨ |
| 198 | MEIDKHSLNIGDYNR | 986-1000 | ▨ | | |
| 199 | HSLNIGDYNRTVGKG | 991-1005 | | | |
| 200 | GDYNRTVGKGPGSRP | 996-1010 | ▨ | | |
| 201 | TVGKGPGSRPQISKE | 1001-1015 | ▨ | | |
| 202 | PGSRPQISKESSMER | 1006-1020 | ▨ | | |
| 217 | MFGVGNTAAQPRGMQ | 1081-1095 | | ■ | |
| 220 | QPPAQPLSSSQPNLR | 1096-1110 | | ■ | |
| 221 | PLSSSQPNLRAQVPP | 1101-1115 | ■ | | |
| 227 | PNNGGLNPLFGPQQV | 1131-1145 | | | |
| 228 | LNPLFGPQQVAMLNQ | 1136-1150 | | | |
| 231 | LSQLNQLSQISQLQR | 1151-1165 | | | |
| 233 | SQLQRLLAQQQRAQS | 1161-1175 | | | ■ |
| 234 | LLAQQQRAQSQRSVP | 1166-1180 | ■ | | |
| 235 | QRAQSQRSVPSGNRP | 1171-1185 | | | |
| 239 | GRPLSVQQQMMQQSR | 1191-1205 | ▨ | | |
| 256 | KEPQSRLRKWTTVDS | 1276-1290 | | ▨ | |
| 257 | RLRKWTTVDSISVNT | 1281-1295 | | ▨ | |
| 263 | FRLEESPFVPYDFMN | 1311-1325 | | | ■ |
| 264 | SPFVPYDFMNSSTSP | 1316-1330 | | | |
| 270 | SPNGSSSVNWPPEFR | 1346-1360 | | | |
| 271 | SSVNWPPEFRPGEPW | 1351-1365 | | | |
| 272 | PPEFRPGEPWKGYPN | 1356-1370 | | | |
| 273 | PGEPWKGYPNIDPET | 1361-1375 | | | |
| 276 | DPYVTPGSVINNLSI | 1376-1390 | | | |
| 279 | NTVREVDHLRDRNSG | 1391-1405 | ▨ | | |
| 280 | VDHLRDRNSGSSSSL | 1396-1410 | | | |
| 287 | PLSSTAQSTSARNSD | 1431-1445 | | | |
| 288 | AQSTSARNSDSKLTW | 1436-1450 | ■ | | |
| 292 | TNTSLAHELWKVPLP | 1456-1470 | | | |
| 293 | AHELWKVPLPPKNIT | 1461-1475 | | | ▨ |
| 294 | KVPLPPKNITAPSRP | 1466-1480 | | | |
| 297 | PPGLTGQKPPLSTWD | 1481-1495 | | | |
| 298 | GQKPPLSTWDNSPLR | 1486-1500 | | | |
| 300 | NSPLRIGGGWQNSDA | 1496-1510 | | | |
| 301 | IGGGWGNSDARYTPG | 1501-1515 | | | |
| 302 | GNSDARYTPGSSWGE | 1506-1520 | | | |
| 303 | RYTPGSSWGESSSGR | 1511-1525 | | ▨ | |
| 304 | SSWGESSSGRITNWL | 1516-1530 | | | |
| 313 | LPHGNALVRYSSKEE | 1561-1575 | | ▨ | |
| 314 | ALVRYSSKEEVVKAQ | 1566-1580 | | | |
| 323 | QSLTPSPGWQSLGSS | 1611-1625 | ■ | | |
| 324 | SPGWQSLGSSQSRLG | 1616-1630 | | ▨ | |
| 335 | YSTSLWGPPSSSDPR | 1671-1685 | | | |
| 336 | WGPPSSSDPRGISSP | 1676-1690 | ■ | | |
| 337 | SSDPRGISSPSPINA | 1681-1695 | | | |
| 338 | GISSPSPINAFLSVD | 1686-1700 | | | |
| 339 | SPINAFLSVDHLGGG | 1691-1705 | ■ | | |
| 340 | AFLSVDHLGGGGESM | 1696-1710 | | | |

MONOCLONAL ANTIBODIES TO RNA BINDING PROTEIN GW182

I. FIELD OF THE INVENTION

The present invention includes heterologous monoclonal antibodies that specifically bind to human GW182 protein, GWBs, and mRNA metabolism. In addition, MAb 2D6 is useful as a diagnostic probe probe of GW182 and GWBs, specifically in archived tissues.

II. BACKGROUND OF THE INVENTION

Many ribonucleoprotein (RNP) particles, such as Sjögren's syndrome antigen A (SS-A/Ro), Sjögren's syndrome antigen B (SS-B/Ia), and components of U2-U6 RNP complexes (first named the Smith (Sm) antigen) have been identified and characterized through the use of human autoantibodies. (1-4) Recently human autoantibodies were used to identify and characterize a novel 182 kDa protein autoantigen named GW182. (5) The GW182 protein contains multiple glycine(G)/tryptophan(W) repeats and a RNA recognition motif (RRM) near the COOH-terminus. This protein was found to be a marker for novel cytoplasmic structures designated GW bodies (GWBs). (5) This protein, which harbors an RNA recognition motif (RRM), was demonstrated to bind a discrete subset of mRNAs from HeLa cells. The GW182 protein binds to a subset of mRNAs and is one of a growing number of messenger ribonucleoproteins (mRNP) that include ELAV/Hu, eIF4E, and polyA binding protein (PABP). (6,7)

A novel autoantigen named GW182 was recently identified when the serum from a patient with a sensory ataxic polyneuropathy was used to immunoscreen a HeLa cDNA library. Unique features of the GW182 protein include 39 repeats of glycine (G) and tryptophan (W) residues, binding to a subset of messenger RNA and localization to unique structures within the cytoplasm that were designated GW bodies (GWBs).

Cytoplasmic proteins associated with mRNA are involved in storing, degrading, transport or stabilization of mRNAs once they are transferred from the nucleus. (6,8-11) These processes have been referred to as components of the ribonome or post-transcriptional operon. (7,9,12) Because the processing and regulation of mRNA is an intense area of research, molecular tools to study GW182 and GW bodies would be valuable reagents. Although human autoantibodies to the GW182 protein and GW bodies are available, they have limited use because they often bind to other intracellular components. Hence, we sought to generate murine monoclonal antibodies (MAbs) to GW182 that could subsequently be used to conduct more thorough studies of GW bodies and their biology in a variety of tissues and species.

It is postulated that the GW182 protein, which contains both a putative RRM domain and nuclear localization signal (NLS)(5), may bind subsets of mRNAs at the nuclear pore complex and then participate in their storage or degradation. The composition of GW bodies as observed by IIF and immunoelectron microscopy, (5) could include other proteins involved in regulation or processing of specific mRNAs. Among the intriguing possibilities is that GW182 and related proteins may be involved in the storage(9,12) or controlled degradation of mRNA.(23,24) Recent reports of cytoplasmic sites of mRNA decapping and degradation bear similarities to structures that contain GW182.(25,26) Pilot studies based on exchange of reagents have suggested that the cytoplasmic structures referred to as stress granules(27) are not present in the HEp2 cells used in these studies nor do the MAbs described here co-localize with markers of stress granules (unpublished observations). Taken together, these observations suggest that the GW182 protein and GWBs are involved in mRNA metabolism and, more specifically, GWBs may be functional sites within the cytoplasm involved in mRNA degradation. Interesting features of the GW182 protein include 39 repeats of glycine (G) and tryptophan (W) residues and its localization in unique cytoplasmic structures that have been designated as GW bodies (GWBs). The GW182 protein, which has an RNA recognition motif and binds specific mRNAs, is thought to be part of a mRNA-protein macromolecular complex. It has been postulated that GWBs provide an additional level of posttranscriptional gene regulation and function in mRNA processing in a cell compartment referred to as the ribosome or posttranscriptional operon [12, 13]. More recent evidence implicates the GW182 protein and GWBs in mRNA degradation pathways [14]. The goal of the present study was to characterize the B-cell immune response in patients with antibodies to GWBs and the GW182 protein which resides within the GWBs and to assess the clinical features of these patients. This is the first report of the clinical features of patients with anti-GWB antibodies and a description of the GW182 epitopes bound by these sera.

Notwithstanding the usefulness of the above-described compositions and methods, a need still exists for monoclonal antibodies that specifically bind to GW182 and to diagnostic assays using those monoclonal antibodies.

III. SUMMARY OF THE INVENTION

This invention provides monoclonal antibodies that specifically bind to GW182, and diagnostic and clinical assays using those compositions.

The identification of autoantigens and the characterization of their respective epitopes are used as diagnostic tools to assist in the clinical evaluation of autoimmune diseases [4, 5, 6]. For example, the presence of autoantibodies to double-stranded DNA and the Sm small nuclear ribonucleoproteins (RNPs) are highly specific serological markers for systemic lupus erythematosus (SLE) [7]. Sjögren's syndrome (SjS) is characterized by the presence of autoantibodies to SS-A/Ro, and/or SS-B/Ia [8]. In addition, the identification of autoantigens and their association with autoimmune disease is a key approach to understanding the autoimmune disease state [9, 10].

Given the following enabling description of the drawings, the inventions should become evident to a person of ordinary skill in the art.

IV. BRIEF DESCRIPTION OF THE DRAWINGS

FIG. 1 shows a summary of epitopes on GW 182 recognized by the monoclonal antibodies of the present invention.

FIG. 2 shows the amino acid sequence and position of the GW182 protein synthetic peptides and their reactivity with three patient sera with anti-GWB antibodies. The gradient of white to black indicates increasing intensity of reaction of antibodies with peptide.

V. DETAILED DESCRIPTION OF THE INVENTION

The present invention is a heterologous monoclonal antibody (MAb) that specifically binds to GW 182 protein or fragments or portions thereof.

Some embodiments of the invention include a heterologous monoclonal antibody (MAb) that binds to one or more epitopes of the GW182 protein. An exemplary list of epitopes is shown in FIGS. 1 and 2. GW182 is a human protein, so heterologous refers to a non-human MAb, e.g., a murine monoclonal antibody.

An embodiment of the invention includes MAb 2D6 and having a deposit number 130204-13, or fragments or portions thereof.

An embodiment of the invention includes MAb 4B6 and having a deposit number 130204-12, or fragments or portions thereof.

An embodiment of the invention includes MAb 5C6 and having a deposit number 130204-14, or fragments or portions thereof.

An embodiment of the invention includes MAb 6D7 and having a deposit number 130204-15, or fragments or portions thereof.

The above noted deposits were made prior to the filing date of the present application in an International Depository Authority as established under the Budapest Treaty. The above noted deposits were deposited in the International Depository Authority of Canada, National Microbiology Laboratory, Health Canada, 1015 Arlington Street, Winnipeg, Manitoba, Canada R3E 3R2.

The present invention also includes the use of one or more of the antibodies, antibody fragments, or functional equivalents noted above in a diagnostic or clinical assay in which GW182 protein may be involved. In preferred embodiments of the invention, the antibody, fragment, or equivalent is used to determine the presence of GW 182 in serum, in vivo or in vitro.

An embodiment of the invention also includes the use of any of the antibodies, fragments, or equivalents thereof to diagnose or treat any disease, syndrome, condition, or indication that involves or is mediated by GW182.

An embodiment of the invention is the use of any of the antibodies, fragments, or equivalents thereof to screen serum, preferably human serum, for the presence of GW182 proteins.

The characterization of a novel panel of MAbs that bind to the GW182 protein and identify GWBs in HEp-2 cells and archived tissues that were subjected to ARM is shown in Table 1. These antibodies are useful in defining the components of the ribonome and the function of the GW182 protein and GW bodies. The ribonome and regulation of gene expression by post-transcriptional processes likely involves various compartments for mRNA processing.(9,12) These MAbs can be used to detect the GW182 protein and GW bodies in the cytoplasm of tissue culture cells by IIF and archived tissues after ARM. In addition, some have the potential to be useful in Western blot and immunoprecipitation of cell extracts. By Western blot analysis, the MAb 4B6 showed the clearest reactivity with a, 180-kDa protein, whereas the MAb 6D7 reacts very strongly with a higher molecular mass protein than the protein identified by the prototype human serum and 4B6. This apparent paradox may have several explanations. One explanation is that the GW182 protein was previously shown to be phosphorylated(5), and it is possible that 6D7 reacts with an epitope that is uniquely exposed on post-translationally modified forms of the GW182 protein.

These MAbs also serve as important reference reagents in a clinical diagnostic setting when it may be necessary to identify sera suspected of having auto-antibodies to the GW182 protein and/or the GW bodies, and have clinical relevance in the identification of patients with Sjögren's syndrome and a subset of patients with neurological diseases.

The availability of MAbs provides useful reagents to confirm the presence of anti-GW182 antibodies in sera and other biological fluids by IIF co-localization, immunoblotting and immunoprecipitation, and other serological assays, such as the laser bead immunoassay described in the examples. The MAbs are specific for, and specifically bind to, the GW182 protein as shown by a number of different assays including the multiplexed laser bead assay and epitope mapping. The pattern of epitope binding by the MAb was quite diverse. MAb 4B6 and 5C6 exhibit the most specific and discrete binding patterns in that they recognized relatively few synthetic peptides. The observation that MAb 2D6 recognized several epitopes is not surprising considering it is an IgM antibody. IgM antibodies are well known to exhibit lower affinity binding and therefore can bind to multiple related epitopes. 2D6 identifies a subset of cells in breast cancer tissue that have features of invasive malignancy.

As used herein, a ligand-binding agent refers to a complementary set of molecules that demonstrate specific binding for each other. A ligand/anti-ligand pair generally binds with relatively high affinity, and for this reason, may be highly desirable for use with the present invention. A very well known ligand/anti-ligand pair is biotin and avidin. As used herein, avidin refers to avidin, streptavidin, neutravidin, derivatives and analogs thereof, and functional equivalents thereof. Avidin may bind biotin in a multivalent or univalent manner. Other exemplary ligand/anti-ligand pairs include, but are not limited to, homophyllic peptides, heterophyllic peptides, "leucine zippers", zinc finger proteins/ds DNA fragment, enzyme/enzyme inhibitor, hapten/antibody, ligand/ligand receptor, and growth factor/growth factor receptor.

As used herein, delivery of the antibody or a composition containing the antibody can occur using a catheter, a microcatheter or by needle and syringe. Delivery by catheter or microcatheter is most often achieved by access through the arterial circuit, however delivery of the solid agent through the venous circuit is also desirable. As an example, the solid agent in the form of particles, coils or stents can be delivered by catheter to the target site using the arterial or venous circuits. Delivery of the solid agent using the arterial circuit is advantageous since the capillary beds downstream of the applied agent in the target tissue act as a means of trapping the agent, thereby preventing the agent from entering the systemic circulation. The solid agent can also be localized within the arterial circulation using a targeting agent associated with the solid agent. Delivery of the solid agent using the venous system is also desirable. Localized delivery of the solid agent in the venous system can be accomplished by binding the solid agent to the target site using a targeting agent associated with the solid agent. The solid agent can also be delivered to the target site during a surgical procedure. As an example, the solid agent in the form of particles can be delivered by syringe and needle to the target site. As a further example, the solid agent in the form of a coil or stent can be placed manually at the target site during the surgical procedure.

As used herein, therapeutically beneficial, providing a therapeutic benefit or the like refers to a desirable change in the physiology of the recipient animal. In a preferred embodiment of the invention, the change is detectable. In accordance with the invention, any biological mechanism that involves activated platelets or platelet modulation may be used or harnessed to achieve a beneficial therapeutic result. Exemplary therapeutic benefits produced in accordance with the present invention include, but are not limited to, forming a thrombus, forming a platelet-mediated occlusion, eliminating a hyperplastic tissue or cells, eliminating a tumor and/or tumor cells, diminishing the size of a hyperplastic tissue, diminishing the size of a tumor, causing the hyperplastic tissue or tumor to become susceptible to additional therapies such as chemotherapy and/or radiation therapy or the like, starving or reducing the nutrient supply to a hyperplastic tissue or cancer, repairing AV-malformations, reducing or preventing blood loss from endoleaks and repairing vessel aneurysms.

As used herein, "administering" refers to any action that results in delivering a composition containing a solid-phase agent to a pre-determined cell, cells, or tissue, typically mammalian. Administering may be conducted in vivo, in vitro, or ex vivo. For example, a composition may be administered by injection or through an endoscope or catheter. Administering also includes the direct application to cells of a composition according to the present invention. For example, during the course of surgery, the vasculature of tumor or hyperplastic tissue may be exposed. In accordance with an embodiment of the invention, the exposed cells or vasculature may be exposed directly to a composition of the present invention, e.g., by washing or irrigating the surgical site, vasculature, and/or the cells.

The solid-phase platelet-binding agent can be localized to a specific target site using a binding or targeting agent. Exemplary binding or targeting agents include, but are not limited to: monoclonal antibodies; polyclonal antibodies; chimeric monoclonal antibodies; humanized antibodies; genetically engineered antibodies; fragments of antibodies, selected from the group consisting of F(ab)2, F(ab')2, Fab, F(ab'), Dab, Fv, sFv, scFv, Fc, and minimal recognition unit; single chains representing the reactive portion of monoclonal antibodies (SC-Mab); tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; a ligand (paired with its complementary anti-ligand); oligonucleotides; any of the above joined to a molecule that mediates an effector function; and mimics or fragments of any of the above. Analogs of the above-listed targeting moieties that retain the capacity to bind to a defined target cell population may also be used within the claimed invention. In addition, synthetic targeting moieties may be designed.

Monoclonal antibodies useful in the practice of the present invention include whole antibodies and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins, which employ sequences from more than one species. See, generally, Kohler and Milstein, Nature, 256:495-97, 1975; Eur. J. Immunol., 6:511-19, 1976. The preferred binding and/or targeting agent capable of localizing the solid-phase agent to a target site is an antibody or antibody-like molecule, preferably a monoclonal antibody. A more preferred binding agent is an antibody that binds a ligand/receptor complex on hyperplastic tissue or cells (e.g., tumor) or the vasculature associated with hyperplastic tissue or cells. The most preferred binding agent is an antibody or antibody-like molecule that binds a growth factor/growth factor receptor complex either on or in the vicinity of the tumor mass such as the tumor vasculature. In a preferred embodiment of the invention, the binding agent (i.e., antibody or antibody-like molecules) would bind to the VEGF/VEGF receptor complex. In a further preferred embodiment of the invention, the antibody or antibody-like molecule binding would recognize a neo-epitope (cryptic or previously unavailable epitope) formed due to ligand/receptor (i.e., growth factor/growth factor receptor) interaction. In a further preferred embodiment of the invention, the binding of the antibody or antibody-like molecules to the growth factor/growth factor receptor complex would not affect the function of either the growth factor or the growth factor receptor.

Oligonucleotides, e.g., anti-sense oligonucleotides that are complementary to portions of target cell nucleic acids (DNA or RNA), are also useful as targeting moieties in the practice of the present invention. Oligonucleotides binding to cell surfaces are also useful.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, such minimal polypeptides exhibiting the binding affinity of the targeting moiety.

The Fv fragments of immunoglobulins have many significant advantages over whole immunoglobulins for the purpose of targeted tumor therapy, including better lesion penetration on solid tumor tissue and more rapid blood clearance, as well as potentially lower Fc-mediated immunogenicity. An exemplary single-chain Fv (scFv) binding agent may be engineered from the genes isolated from the variable regions of antibodies recognizing a ligand/receptor complex.

Any composition that includes a monoclonal antibody of the present invention with or without a targeting agent according to the invention may be used in vivo or in vitro in a clinical or diagnostic assay. The composition may include one or more adjuvants, one or more carriers, one or more excipients, one or more stabilizers, one or more permeating agents (e.g., agents that modulated movement across a cell membrane), one or more imaging reagents, one or more effectors; and/or physiologically-acceptable saline and buffers. Generally, adjuvants are substances mixed with an immunogen in order to elicit a more marked immune response. The composition may also include pharmaceutically acceptable carriers. Pharmaceutically acceptable carriers include, but are not limited to, saline, sterile water, phosphate buffered saline, and the like. Other buffering agents, dispersing agents, and inert nontoxic substances suitable for delivery to a patient may be included in the compositions of the present invention. The compositions may be solutions suitable for administration, and are typically sterile, non-pyrogenic and free of undesirable particulate matter. The compositions may be sterilized by conventional sterilization techniques.

In a preferred embodiment of the invention, a suitable composition includes a binding or targeting agent that binds to ligand/receptor complex. Exemplary antigens useful as targets in accordance with the present invention include, but are not limited to, antigens associated with cancer, including, lung, colon, rectum, breast, ovary, prostate gland, head, neck, bone, immune system, blood, or any other anatomical location. Exemplary antigens and/or pre-determined sites include but are not limited to VEGF/VEGF receptor complex, FGF/FGF receptor complex, or TGF.beta/TGF.beta receptor complex, p-selectin, sialyl-lewis X, endothelin, endothelin receptor, endothelin/endothelin receptor complex, alpha-fetoprotein, platelet-endothelial cell adhesion molecule (PECAM), CD31, CD34, CD36, glycoprotein 1b (GP1b), endoglin, thrombomodulin, endothelial leukocyte adhesion molecule (ELAM), intercellular adhesion molecule 1 (ICAM-1), MHC-I, and MHC-II. The subject may be a human or animal subject.

In accordance with a method of the invention, the binding agent must be capable of binding a ligand/receptor complex, and may be administered to the patient by any immunologically suitable route. For example, the binding agent may be introduced into the patient by an intravenous, intra-arterial, subcutaneous, intraperitoneal, intrathecal, intravesical, intradermal, intramuscular, or intralymphatic route. The composition may be in solid, solution, tablet, aerosol, or multi-phase formulation forms. Liposomes, long-circulating liposomes, immunoliposomes, biodegradable microspheres, micelles, or the like may also be used as a carrier, vehicle, or delivery system. Further more, using ex vivo procedures well known in the art, blood, plasma or serum may be removed from the patient; optionally, it may be desirable to purify the antigen in the patient's blood; the blood or serum may then be mixed with a composition that includes a binding agent or the solid-phase agent according to the invention; and the treated blood or serum is returned to the patient. The clinician may compare the responses associated with these different routes in determining the most effective route of administration. The invention should not be limited to any particular method of introducing the binding agent into the patient.

Administration may be once, more than once, or over a prolonged period. As the compositions of this invention may be used for patients in a serious disease state, i.e., life-threatening or potentially life-threatening, excesses of the solid-phase agent may be administered if desirable. Actual methods and protocols for administering pharmaceutical compositions, including dilution techniques for injections of the present compositions, are well known or will be apparent to one skilled in the art. Some of these methods and protocols are described in Remington's Pharmaceutical Science, Mack Publishing Co. (1982).

A solid-phase agent may be administered in combination with other binding agents, or may be administered in combination with other treatment protocols or agents, e.g., chemotherapeutic agents, embolizing agents such as Gelfoam or polyvinyl alcohol (PVA) particles or the like.

As is well known in the art, a disadvantage associated with administering treatment agents or treatment agent conjugates in vivo includes non-target or undesirable target binding. It is therefore a desirable attribute of any administered composition to minimize non-target binding, to minimize non-target exposure to the treatment agent or active agent, and/or to maximize clearance of non-bound binding agent, ligand, or active agent. Moreover, optimizing these attributes typically permits administering a higher dose of active agent, a therapeutic agent, or an element of the process that activates a previously un-activated agent. Those skilled in the art are well versed in selecting the optimal parameters for administering the highest possible dose while remaining safely below a toxic threshold.

compositions and methods of the present invention include any mechanism of delivering a composition to the pre-selected site, including but not limited to systemically, locally, orally, or topically.

VI. EXAMPLES

Example 1

Serum and Antibodies

The index human serum was from a Caucasian woman who had a mixed motor and sensory polyneuropathy. This serum was selected based on its reactivity to an apparently unique cytoplasmic domain and it was used to isolate the original GW182 cDNA.(5) A polyclonal rabbit antibody directed to GW182 was produced as previously published.(5)

Example 2

Indirect Immunofluorescence (IIF)

The presence of anti-GW182 antibodies was first identified on HEp-2 cell substrates (ImmunoConcepts Inc., Sacramento, Calif.) by indirect immunofluorescence (IIF) using techniques as previously described.(13,14) Secondary antibodies included Cy3 conjugated goat anti-human IgA, IgG, IgM, and fluorescein isothiocyanate (FITC) conjugated affinity purified goat antimouse IgG, IgM (Jackson ImmunoResearch, West Grove, Pa.). Co-localization of the index human serum and the murine antibodies was conducted using a Leica DM RXA2 microscope with the appropriate FITC, Cy3, and DAPI filter sets. Images were captured with a Princeton Instruments digital camera and processed in Adobe Photoshop version 5.5.

Example 3

Antigen Retrieval Method (ARM)

Archived human cancer tissues that were fixed and embedded in paraffin by conventional histopathology techniques were obtained from the Department of Pathology at The Scripps Research Institute (La Jolla, Calif.). Five- to eight-micron sections were floated onto Superfrost Plus glass slides (Fisher Scientific, Springfield, N.J.) and allowed to dry on a warm plate set at 37° C. The paraffin was removed through three changes of xylene at room temperature for 5 min and the sections were then brought to distilled water through a graded series of ethanol (100, 95, and 75%). The slides were rinsed in two changes of deionized water and then immersed in 250 mL of an antigen retrieval solution AR-10 (Biogenex, San Rámon, Calif., cat. # HK057-5K). The slides were placed in a plastic holder, transferred into a microwave pressure cooker (NordicWare, Minneapolis, Minn.) and subjected to 800-850 W of power for 15 min. The power was then reduced to 300-350 W and the microwave treatment continued for an additional 15 min. The slides were removed from the pressure cooker after the solution had cooled and incubated in phosphate-buffered saline (PBS: 0.01 M sodium phosphate buffer, 0.15M NaCl, pH 7.3) at room temperature for 30 min. The tissues on the slides were then overlaid with the primary antibody diluted in PBS, a cover slip was placed on top of the solution, and they are incubated over night at 4° C. The primary antibody was then removed in three changes of PBS and processed for IIF as described above.

Example 4

Recombinant Protein Production and Generation of Mouse MAbs

The cDNA insert encoding a partial length GW182 protein (5) was subcloned into the expression vector pET28 (Novagen, Wis.) and transformed to *E. coli* JM109 (DE3) for recombinant protein production. The N-terminal 63 histidine fusion recombinant protein was purified from a 1-L culture using Ni21 affinity chromatography as per the manufacturer's instructions (Qiagen, Valencia, Calif.). Mice were then immunized by injections of 10 mg of the purified recombinant protein (100-mL volume of antigen) in an equal volume of Freund's complete adjuvant followed by two subsequent injections of protein in Freund's incomplete adjuvant. The production of anti-GW182 was monitored by IIF of serum as described above and when high titers of antibodies were observed, the mice were sacrificed, the spleens removed and processed to produce MAbs. The spleen cells were fused to Sp2/mIL6 myeloma cells at a ratio of approximately 5:1 in the presence of 40% polyethylene glycol (PEG)1500. The hybridoma cells were selected using Dulbecco's modified Eagle's minimal essential medium (DMEM) medium that contained 20% fetal bovine serum (FBS), hypoxantine, aminopterine, and thymidine (HAT) (100 mM sodium hypoxanthine, 0.4 mM aminopterin, and 16 mM thymidine), OPI (2.2 mM oxalacetic acid, 0.1 mM sodium pyruvate, and 0.4 U bovine insulin/mL), 10 mM HEPES, 10% NCTC-109 medium, 55 mM beta-mercaptoethanol, 1× antibiotic/antimycotic (Gibco, Grand Island, N.Y.) and gentamicin (50 mg/mL).

Example 5

In vitro Transcription/Translation and Immunoprecipitation

The full-length GW182 cDNA(5) was used as a template for in vitro transcription and translation (TnT, Promega, Madison, Wis.) in the presence of [35S]-methionine at 30° C. for 1.5-2 h. (5,14) Immunoprecipitation (IP) of the in vitro translated products was prepared by incubating 100 mL of a 10% (v/v) suspension of protein G-Sepharose beads (Pharmacia, Uppsala, Sweden) with 10 mL of the MAbs, 500 mL of NET2 buffer [50 mM Tris-HCl, pH 7.4, 150 mM NaCl, 5 mM ethylene-diaminetetraacetic acid (EDTA), 0.5% N onidet P-40, 0.5% deoxycholic acid, 0.1% SDS, 0.02% sodium azide] and 10 mL of labeled protein was added. After a 2-h incubation period at 4-8° C., the beads were washed five times in NET2. For the MAb 2D6, a preincubation step was done with 100 mL of unconjugated IgG affinity purified goat anti-mouse IgG, IgM (Jackson ImmunoResearch Lab, West Grove, Pa.), 500 mL NET2, and 100 mL protein G Sepharose beads for 1 h at 4° C. The bound antibody-antigen complexes were eluted with 10 mL of sodium dodecyl sulfate polyacrylamide gel electrophoresis (SDS-PAGE) sample buffer and analyzed by SDSPAGE as described. (15)

Example 6

Western Blot

HeLa cell extracts were obtained and fractioned on a 10% SDS-PAGE, which was then transferred to nitrocellulose, as previously described. (14) Human and rabbit sera, and MAbs were diluted or added neat to the nitrocellulose strips for 1 h. Following washing with PBS-Tween, horseradish peroxidase (HRP)-conjugated antibodies, either goat anti-rabbit, goat antihuman or goat anti-mouse were diluted according to the manufacturer's instructions and applied to the strips for one hour at room temperature. Subsequent reactivity was then detected using the enhanced chemiluminescence (ECL) kit (Amersham Biosciences, Baie d'urfe, Quebec).

Example 7

Epitope Mapping

Solid phase peptides were prepared as described elsewhere. (16-18) Briefly, sequential peptides of 15 amino acids offset by 5 amino acids were synthesized to represent the entire length of the GW182 protein. Immunoblotting was carried out by first soaking the membrane in TBS (10 mM Tris/Cl pH7.6, 150 mM NaCl) and then blocked with 2% milk/TBS. Mouse MAb supernatants were diluted [1/10] in 2% milk/TBS and applied to the membrane. After 2 h of incubation at room temperature, the membrane was washed three times at 5-min intervals with TBS. Secondary antibody to HRP-conjugated anti-mouse antibodies (Jackson ImmunoResearch Lab) was diluted according to the manufacturer's protocol and the reaction was visualized using ECL Western blotting detection reagents (Amersham International). After the sequences of the reactive epitopes were identified, a BLAST search of all genomes was conducted to identify homologous sequences in other proteins.

Example 8

Laser Bead Immunoassay

Addressable laser beads (Luminex Corp., Dallas, Tex.) were obtained and processed as described. (19-22) An appropriate set of spheres (Luminex Corp.) bearing laser reactive dyes were selected for coupling the recombinant purified GW182. Unless specified, all incubations and reactions were at room temperature. Ten micrograms of 1-ethyl-3-(3-dimethylaminopropyl) carboiimide hydrochloride (EDC, Pierce Rockford, Ill.) and Nhydroxysuccinimide (NHS, Pierce) were placed in separate microcentrifuge tubes (USA Scientific, Inc.) and dissolved in 200 mL of activation buffer (0.1 M sodium phosphate, pH 7.2). One hundred microliters of the laser bead suspension was placed into a microcentrifuge tube and centrifuged at 10,000 rpm in an Eppendorf microfuge for 1 min and the fluid decanted. Forty microliters of activation buffer was added to the pelleted beads and they were gently resuspended by brief sonication and vortexing. Five microliters of the EDC and NHS were added in sequence to the resuspended microspheres, followed by brief sonication and vortexing. The suspended spheres were incubated in the dark for 20 min before the protein of interest, dissolved in PBS coupling buffer (0.01 M NaPO4, 0.14 M NaCl, pH, 7.3), was added to the mixture. After an additional incubation in the dark for 3 min, the suspension was centrifuged at 13,000 rpm for 3 min. The fluid was decanted and 125 mL of coupling buffer was added. The spheres were resuspended by sonication and vortexing as above before repelleting by centrifugation at 13,000 rpm for 3 min. The supernatant was decanted, 125 mL of the protein solution (50 mg/mL) added and the beads resuspended by sonication and vortexing. The suspension was incubated for 1 h at room temperature in the dark. The protein-coupled microspheres were pelleted by centrifugation at 10,000 rpm for 2 min and then resuspended in 125 mL of washing buffer (PBS-T: PBS pH 7.2, 0.05% Tween 20). After two cycles of resuspension and pelleting in 125 mL of blocking/storage buffer (0.5% BSA in PBS), the beads were stored as a suspension in 100 mL of blocking buffer at 2-8° C. until required for use. MAbs were diluted in QUANTA Plex sample diluent (Inova, San Diego, Calif.) to a final dilution of 1/1000. To each well 40 mL of bead stock (1 part microspheres in blocking buffer to 40 parts sample diluent) and 10 mL of diluted MAbs were added. The microwell plate was then placed on an orbital shaker and incubated for 30 min. To this mixture, 50 mL of the tagged phycoerythrin conjugated secondary goat anti-mouse antibody (Jackson Laboratories) was added at a [1/50] dilution. The reactivity obtained was read using the Luminex 100 (Luminex Corp.) and compared with binding of an irrelevant MAb control (golgin97: Molecular Probes, Eugene, Oreg.).

Example 9

RESULTS

We set out to develop a panel of mouse MAbs that would detect the GW182 protein and recognize GWBs.(5) Fifty candidate clones were identified when supernatants derived from the mouse splenocyte fusions were initially screened by enzyme-linked immunoadsorbant assay (ELISA) using a GW182 protein, and then for the distinctive cytoplasmic IIF pattern observed with the index human serum. Four MAbs designated 4B6, 5C6, 6D7, and 2D6 were selected for further study and characterization based on co-localization with the index human serum. Among the four MAbs, 4B6 displays a staining pattern that is most representative of the IIF pattern observed with the index human serum. The serological features of the MAbs, including their antibody isotypes, are summarized in Table 1. All of the MAbs were IgG isotypes except for 2D6, which was an IgM antibody. We have established that the MAbs stain cells and tissues from other species including mouse, rabbit, chicken, frog, and Drosophila sp. (data not shown). We next examined whether the MAbs bound to GW182 and GWBs in paraffin-embedded breast cancer tissues after application of the ARM technique. The best results were obtained with MAb 2D6, which reacted very strongly with GWBs in a subset of cells in the cancer tissue. This staining was compared with a parallel section stained with conventional hematoxylin and eosin. The specificity of reactivity of MAb 2D6 was supported when we showed that this reactivity co-localized with the staining produced by the index human serum (data not shown). Confirmation that all four mouse MAbs recognize the GW182 protein was demonstrated by immunoprecipitation of the radiolabeled recombinant protein. In this assay, the MAb 2D6 showed weaker reactivity when compared to the other MAbs. However, by Western blot analysis, 2D6 bound the partial-length 62-kDa recombinant GW182 protein as did the other MAbs (Table 1). The Western blot analysis using HeLa cell extracts showed that only 4B6 and the index human serum clearly recognized a ~180-kDa protein of the expected MW of the full length GW182 protein. The 2D6 and 5C6 MAbs reacted weakly with a ~180-kDa protein and more clearly with at least two other higher molecular weight proteins. MAb 6D7 reacted very strongly with a ~200-kDa protein.

The final confirmation that the MAbs bound to GW182 was demonstrated by the multiplexed laser bead assay. As shown in Table 1, all of the MAbs bound to the purified partial length GW182 protein in this assay. The level of reactivity (calculated as units of fluorescence) was higher than that seen with the index human sera and much higher than the negative control MAb directed to golgin 97.

The membrane consists of a 15-mer peptide from the full-length protein that is offset by 5 amino acids from the peptides to the immediate right and left. The epitopes recognized by the MAbs in this assay are summarized in FIG. 1. As expected, the MAbs reacted with relatively few epitopes. For example, MAbs 2D6 and 5C6 reacted strongly with epitopes encompassed by amino acids 586-605. MAb 2D6 also reacted with other nonoverlapping epitopes. In addition to its major reactivity to regions 586-605, MAb 5C6 displayed minor reactivity to the regions 626-640. In contrast, MAb 4B6 reacted strongly with peptides represented by aa 621-645. MAb 6D7 recognized peptides that, for the most part, do not overlap with the other MAbs (i.e., amino acids 791-815). When a BLAST search set to a cutoff of 60% similarity over the entire length of the peptide was conducted, only the GW182 protein and related ESTs, KIAA1460, KIAA1582, and KIAA1093, showed identity to the epitopes bound by the MAbs. This provided additional evidence that these MAbs are specific for the GW182 protein.

Example 10

The goal of the present study was to identify the clinical features of patients with anti-GW182 antibodies and to characterize the B cell anti-GW182 response by defining the epitopes bound by human autoantibodies. The most common clinical diagnosis of patients with anti-GW182 antibodies was Sjögren's syndrome followed by mixed motor/sensory neuropathy, and systemic lupus erythematosus. Of interest, 5 (28%), 9 (50%), and 3 (17%) of the 18 sera that react with GWBs had autoantibodies to the GW182 and the 52 kDa and 60 kDa SS-A/Ro autoantigens, respectively. Epitopes bound by the human autoantibodies were mapped to the GW-rich middle part of the protein, the non-GW rich region, and the C-terminus of GW182 protein. None of the GW182 epitopes had significant sequence similarities to other known proteins. GW182 represents a new category of ribonucleoprotein autoantigens.

Example 11

Materials and Methods

Patient Serum and Antibodies

All human sera used in this study were obtained from serum banks at the advanced Diagnostics Laboratory (University of Calgary, Calgary, Canada), the W. M. Keck Autoimmune Disease Center (Scripps Research Institute, La Jolla, Calif., USA), and Juntendo University (Tokyo, Japan). The index human serum used in this study was selected based on its reactivity to an apparently unique cytoplasmic domain and its reactivity with the native and recombinant GW182 protein [5]. Clinical information was obtained by contacting the referring physician and retrospective chart review. Indirect immunofluorescence The presence of anti-GW182 antibodies in the human sera were initially tested by Indirect immunofluorescence (IIF) using HEp-2 cell substrates (Immuno Concepts, Sacramento, Calif., USA) and had a cytoplasmic staining pattern that was characteristic of anti-GWB antibodies [5]. Reactivity with GWBs was confirmed by IIF colocalization studies on HEp-2 cells where a monoclonal antibody (4B6) to the recombinant GW182 protein which stains GWBs was used as the marker antibody [28]. Secondary antibodies for colocalization studies were fluorescein isothiocyanate conjugated anti-mouse IgG (Jackson ImmunoResearch, West Grove, Pa., USA) and fluorescein isothiocyanate or Cy3-conjugated anti-human IgG (Jackson ImmunoResearch). Nuclei in the cell substrates were stained with 40,6-diamidino-2-phenylindole that was included in the glycerol mounting medium (VectaShield, Vector, Burlingame, Calif., USA).

In vitro Transcription/Translation and Immunoprecipitation

Reactivity of the sera with recombinant GW182 protein was confirmed by immunoprecipitation (IP) of the recombinant protein. The full-length GW 182 cDNA was used as a template to synthesize the protein in an in vitro transcription and translation (TnT) protocol that used a rabbit reticulocyte lysate kit (TnT, Promega Biotec, Madison, Wis., USA) in the presence of [35S]methionine at 30° C. for 3-4 h as previously described [5]. To confirm the presence of TnT products 2- to 5-μl samples were separated by sodium dodecyl sulfate (SDS) polyacrylamide gel electrophoresis and analyzed by autoradiography. The TnT products were then used in IP reactions by combining 100 μl of a 10% protein A Sepharose bead suspension (Sigma, catalog no. P-3391), 10 μl human serum, 500 μl NET2 buffer (50 mM Tris-HCl, pH 7.4, 150 mM NaCl, 5 mM EDTA, 0.5% Nonidet P-40, 0.5% deoxycholic acid, 0.1% SDS, 0.02% sodium azide), and 10 μl of radiolabeled protein product. After incubation for 1 h at 4-8° C. the suspension was washed five times in NET2, the proteins eluted in 10 µl sample buffer, and analyzed by 10% gel SDS polyacrylamide gel electrophoresis as described [15].

Epitope Mapping

Epitope mapping employed sequential peptides of 15 amino acids offset by five amino acids, representing the full-length GW182 protein, were synthesized on membranes using the SPOT technology as previously described [17, 29]. The membranes containing the peptides were processed for immunoblotting by soaking the membrane in Tris-buffered saline (TBS; 10 mM Tris-HCl pH7.6, 150 mM NaCl) for 10 min and then blocking with 2% milk/TBS for 1 h at room temperature. The human sera were diluted 1/100 in 2% milk/TBS and applied to the membrane. After 2 h of incubation at room temperature the membrane was washed three times with TBS. A horseradish-peroxidase conjugated goat anti-human IgG (Jackson ImmunoResearch) was diluted according to the manufacturer's protocol, and reactivity was visualized using enhanced chemiluminescence western blotting detection reagents (Amersham International). After reactive epitopes were identified a BLAST search of the GenBank using the reactive sequences as the query was conducted to identify homologous sequences in other proteins.

Purified Recombinant GW182

The GW182 cDNA insert encoding a partial length of the GW182 protein was subcloned into pET28 (Novagen, Madison, Wis., USA). *Escherichia coli* JMI09 (DE3) was transformed with this subclone, and the recombinant protein produced was purified using Ni2+ affinity chromatography as per the manufacturer's instructions (Qiagen, Valencia, Calif., USA). This recombinant protein was subsequently used in the laser bead immunoassay described below.

Laser Bead Immunoassay

A set of addressable beads bearing laser reactive dyes (Luminex, Austin, Tex., USA) were selected to couple the recombinant purified GW182 protein. Unless otherwise specified, all incubations and reactions were conducted at room temperature. Ten micrograms of 1-ethyl-3-(3-dimethylaminopropyl) carboiimide hydrochloride (Pierce, Rockford, Ill., USA) and N-hydroxysuccinimide (Pierce) was placed in separate microcentrifuge tubes (USA Scientific) and dissolved in 200 µl activation buffer (0.1 M sodium phosphate, pH 7.2). Of the laser bead suspension 100 µl was placed into a microcentrifuge tube and centrifuged at 10,000 rpm in a microcentrifuge for 1 min, and the fluid was decanted. Forty microliters of activation buffer was added to the pelleted beads, and they were gently resuspended by brief sonication and vortexing. Five microliters of 1-ethyl-3-(3-dimethylaminopropyl) carboiimide hydrochloride and N-hydroxysuccinimide was added in sequence to the resuspended microspheres, followed by brief sonication and vortexing. The suspended spheres were incubated in the dark for 20 min before the purified recombinant GW182 protein, dissolved in coupling buffer (0.14 M NaCl, 0.01 M NaPO4, pH approx. 7.2: PBS), was added to the mixture. After an additional incubation in the dark for 3 min, the suspension was centrifuged at 13,000 rpm for 3 min. The fluid was decanted and 125 µl coupling buffer added. The spheres were resuspended by sonication and vortexing as above before repelleting by centrifugation at 13,000 rpm for 3 min. The supernatant was decanted, 125 µl the protein solution (50 µg/ml) added, and the beads resuspended by sonication and vortexing. The protein and sphere suspension were incubated for 1 h at room temperature in the dark. The protein-coupled microspheres were pelleted by centrifugation at 10,000 rpm for 2 min and then resuspended in 125 µl washing buffer (PBS pH 7.2, 0.05% Tween 20). After two cycles of resuspension and pelleting in 125 µl blocking/storage buffer (0.5% BSA in PBS), the beads were stored as a suspension in 100 µl of blocking buffer at 2-8° C. until required for use. To analyze reactivity of the sera with the bound GW182, patient sera were diluted in Quanta Plex sample diluent (INOVA, San Diego, Calif., USA) to a final dilution of 1/1,000. To each well 40 µl of bead stock (1 part microspheres in blocking buffer to 40 parts Quanta Plex sample diluent) and 10 µl of diluted patient sera were added and incubated for 30 min on an orbital shaker. Then 50 µl phycoerythrin-conjugated goat anti-human IgG (Jackson ImmunoResearch) diluted 1/50 was added to each well and incubated on the orbital shaker for an additional 30 min. The reactivity of the antigen-coated beads was determined on a Luminex 100 dual-laser flow cytometer (Luminex). Control negative and standard positive sera were included in each assay. The tests were semiquantitative, and the results were expressed as median fluorescent intensity of the test sample.

Line Immunoassay

The serum samples were tested for reactivity to other autoantigens using a "line" assay that includes recombinant and native SmB, SSA/Ro52, SS-A/Ro60, SS-B/Ia, U1-RNP, Scl-70, ribo P antigens located on a solid phase strip (INNO-LIA, Innogenetics, Norcross, Ga., USA). The assays were performed according to the manufacturer's instructions, and at the completion of the assay the strips were dried and were interpreted based on visual comparison of the intensity of the bands on the test strip to the cutoff control on another strip.

Example 12

Results

IIF using the index human serum on HEp-2 cells showed a pattern of distinctive cytoplasmic dots and what was previously described as GWBs. The number of GWBs present in HEp-2 cells varied from zero in mitotic cells to more than 30 in interphase cells. Previously it was shown that GWBs containing the GW182 autoantigen are distinguished from other cytoplasmic organelles, including the Golgi complex, lysosomes, endosomes, and proteasomes [5]. Over a 14-month period the clinical reference laboratory (Advanced Diagnostics Laboratory, University of Calgary) received approximately 5,000 sera for autoantibody analysis as requested by physicians who were investigating the presence of autoimmune disease, such as SLE and SjS, in their patients. From these 5,000 serum samples approx. 200 sera showed a cytoplasmic speckled staining pattern on HEp-2 cells. Of these 200 sera 18 (9%) had autoantibodies to the GWBs as determined by colocalization with the monoclonal antibody 4B6 that reacts with the GW182 protein and stains the GWBs. The other sera had antibodies to early endosome antigen 1, ribosomal RNP, mitochondria, cytoplasmic linker protein (CLIP-170), and other as yet unknown endosome or lysosome antigens. None of the 18 sera that bound GWBs had antibodies to dsDNA, chromatin, U1-RNP, topoisomerase I (Scl-70), fibrillarin (U3 RNP), or centromeres/kinetochores [30]. The immunoglobulin isotype of all sera with antibodies to GWBs was IgG as shown by isotypespecific staining of HEp-2 cells, immunoblotting, and protein A Sepharose immunoprecipitation of recombinant GW182 protein. The anti-GWB titers as determined by IIF on HEp-2 cell substrates ranged from 1/320-1/5, 120.

A study of 2500 healthy female blood donors showed that none of these samples contained anti-GWB antibodies as determined by IIF using HEp-2 cells. Although all 18 sera had antibodies to the GW body, the multiplexed laser bead assay indicated that 4 of the 18 sera (nos. 1, 3, 9, 10) recognized the recombinant GW182 protein which is one of several proteins fourid within GWBs (Table 2). When the reactivity of the 18 sera was also tested by IP using in vitro transcribed/translated protein, it was observed that 4 sera (nos. 1, 3, 8, 10) IP the GW182 protein. Therefore when the data of the two assays that used recombinant protein are combined, 5 of the 18 sera ecognized GW182.

The clinical data obtained on the 18 patients who had the GWB staining pattern are summarized in Table 1. Of the 18 patients 17 (39%) with autoantibodies to the GWBs were women and ranged in age from 46 to 85 years (mean 58). The clinical diagnoses could be stratified into three groups: group A composed of 9 patients had predominantly mixed motor and/or sensory neuropathy, although other disease manifestations were also noted; 3 patients in group B had SjS in addition to some neurological features that overlapped with group A; in group C there were 6 patients who had SLE and/or SjS without documented evidence of neurological disease. When the various diagnoses or clinical conditions were tabulated individually, SjS was the most common, seen in 7 of 18 (39%), followed by patients with neurological disease (motor and sensory neuropathy and/or ataxia) in 6 (33%), followed by SLE in 4 (22%). When it was observed that some of the patients had SLE and SjS, we were interested to determine whether autoantibodies to known autoantigens that are typical markers of SLE and SjS were present. Autoantibodies to SS-A/Ro and SS-B/Ia were correlated with the diagnosis of SjS in 6/7 patients diagnosed with SjS (Table 2). However, four patients in group A had anti-SSA/Ro52 antibodies but did not have a clinical diagnosis of SjS or SLE. Interestingly, 9 sera had antibodies to the 52-kDa SS-A/Ro antigen, but 7 did not have coexisting antibodies to the 60 kDa SS-A/Ro antigen. One patient (no. 4) had a malar rash, arthralgia, and antibodies to the SmB protein but did not fulfill criteria for classification as definite SLE.

Only 4 of the 18 patient sera (22%; nos. 1, 3, 8, 10) with anti-GWB antibodies as defined by colocalization, IP the GW182 protein. Three of these four sera (nos. 1, 3, 10; Table 2) were used for epitope mapping due to limited quantity available for the fourth serum (no. 8). Multiple epitopes over the entire length of GW182 were recognized by the patient sera (FIG. 2). Four overlapping reactive peptides were shared between patient no. 1 and patient no. 10: amino acids 666-695, 951-970, 1676-1690, 1691-1705. Several peptides were in common between patient no. 1 and patient no. 3: amino acids 431-450, 766-780, 921-945, 951-970, 1101-1115, 1161-1185, 1191-1205, 1391-1410, 1431-1445, 1616-1630. Interestingly, only one peptide (1511-1525) was bound by both patient no. 10 and patient no. 3. The reactive epitopes mapped to the GW-rich, the middle portion, the non-GW rich, and the C-terminal domains of the GW182 protein (FIG. 2). When the reactive peptides were subjected to a BLAST analysis, only the published GW182 protein and related EST clones, KIAA1460, KIAA1582, and KIAA1093 showed more than 60% amino acid sequence identity. The KIAA1460 EST is known to be partial-length GW182 [5].

Our study shows that multiple epitopes of the GW182 protein are recognized by the human antibodies. The SPOT method of epitope mapping has been validated, and the majority of studies has shown that each patient displays an individual epitope pattern. The diverse and heterogenic epitope recognition pattern among the patients observed in this study is not unlikely since the fine specificity of B-cell immune processes strongly depends on the MHC system. Epitope mapping followed by BLAST analysis confirmed that the autoantibody targets are unique to the GW182 protein because sequence similarity to other known eukaryotic or prokaryotic proteins or expressed sequence tags was not observed. This suggests that the GW182 protein drives the autoimmune response and reactivity to endogenous or exogenous proteins with similar sequence motifs and molecular mimicry is less likely. This also raises the possibility that, as with many other autoantibody systems, autoreactivity to GW182 demonstrates intramolecular epitope spreading.

The association of anti-GWB antibodies with antibodies to the 52 kDa SS-A/Ro antigen, particularly in the patients with no evidence of SjS and SLE was an unexpected finding. Although the 52-kDa SS-A/Ro antigen has been localized to both the nucleus and cytoplasm, antibodies from a variety of sources directed to the 52-kDa SS-A/Ro autoantigen do not produce a GWB staining pattern. The function of the 52 kDa SS-A/Ro antigen is not clear, and the observation that it is associated with GWB antibodies may help clarify its function.

In summary, GWBs are a novel class of RNP autoantigens that are specifically recognized by human autoantibodies. Over the past three decades several autoantigens that are part of RNP macromolecular complexes have been described, and we propose that autoantibodies to GWBs and GW182 now join this growing list [29]. Some of these autoantigens, including Sm, U1-RNP, and Hu, have been shown to have a central role in mRNA splicing, mRNA processing, and mRNA translation. In this study we observe that the diseases associated with autoantibodies to GWBs overlap with those associated with other RNPs but extend to patients who appear to have primary neurological disorders.

REFERENCES

1. Tan E M: Autoantibodies in pathology and cell biology. Cell 1991;67:841-842.
2. Lerner M R and Steitz J A: Snurps and scyrps. Cell 1981; 25:298-300.
3. Craft J: Antibodies to snRNPs in systemic lupus erythematosus. Rheum Dis Clin N A 1992;18:311-335.
4. Luhrmann R: Functions of U-snRNPs. Mol Biol Rep 1990; 14:183-192.
5. Eystathioy T, Chan E K L, Tenenbaum S A, Keene J D, Griffith K J, and Fritzler M J: A phosphorylated cytoplasmic autoantigen, GW182, associates with a unique population of human mRNAs within novel cytoplasmic speckles. Mol Biol Cell 2002;13:1338-1351.
6. Tenenbaum S A, Carson C C, Lager P J, and Keene J D: Identifying mRNA subsets in messenger ribonucleoprotein complexes by using cDNA arrays. Proc Natl Acad Sci USA 2002;97:14085-14090.
7. Tenenbaum S A, Lager P J, Carson C C and Keene J D: Ribonomics: identifying mRNA subsets in mRNP complexes using antibodies to RNA-binding proteins and genomic arrays. Methods 2002;26:191-198.
8. Keene J D: Why is Hu where? Shuttling of early-response-gene messenger RNA subsets. Proc Natl Acad Sci USA 1999;96:14085-14090.
9. Keene J D: Ribonucleoprotein infrastructure regulating the flow of genetic information between the genome and proteome. Proc Natl Acad Sci USA 2001;98:7018-7024.
10. Brennan C M and Steitz J A: HuR and m RNA stability. Cell Mol Life Sci 2001;58:266-277.
11. Paushkin S, Gubitz A K, Massenet S, and Dreyfuss G: The SMN complex, an a ssemblyosome of ribonucleoproteins. Curr Opin Cell Biol 2002;14:305-312.
12. Keene J D and Tenenbaum S A: Eukaryotic mRNPs may represent posttranscriptional operons. Mol Cell 2002;9: 1161-1167.
13. Fritzler M J: Immunofluorescent antinuclear antibody test. In: Manual of Clinical Laboratory Immunology, Rose N R, de Macario E C, Folds J D, Lane C L, and Nakamura R M (Eds), ASM Press, Washington, D.C., 1997, 920-927.
14. Fritzler M J, Lung C-C, Hamel J C, Griffith K and Chan E K L: Molecular characterization of golgin-245: A novel Golgi complex protein containing a granin signature. J Biol Chem 1995;270:31262-31268.
15. Laemmli U K: Cleavage of structural proteins during the assembly of the head of bacteriophage T4. Nature 1970; 227:680.
16. Frank R and Overwin H: SPOT synthesis. Epitope analysis with arrays of synthetic peptides prepared on cellulose membranes. Methods Mol Biol 1996;66:149-169.
17. Mahler M, Mierau R, and Bluthner M: Fine-specificity of the anti-CENP-A B-cell autoimmune response. J Mol Med 2000;78:460-467.
18. Frank R: The SPOT synthesis technique. Synthetic peptide arrays on membrane supports—principles and applications. J Immunol Methods 2002;267:13-26.
19. Iannone M A, Consler T G, Pearce K H, Stimmel J B, Parks D J, and Gray J G: Multiplexed molecular interactions of nuclear receptors using fluorescent micorspheres. Cytometry 2001;44:326-337.
20. Bellisario R, Colinas R J, and Pass K A: Simultaneous measurement of antibodies to three HIV-1 antigens in newborn dried blood-spot specimens using a multiplexed microsphere-based immunoassay. Early Hum Dev 2001; 64:21-25.
21. Willman J H, Hill H R, Martins T B, Jankowski T D, Ashwood E R, and Litwin C M: Multiplex analysis of heterophil antibodies in patients with intermediate HIV immunoassay results. Am J Clin Pathol 2001;115:764-769.
22. Vignali D A: Multiplexed particle-based flow cytometric assays. J Immunol Meth 2000;21:243-255.
23. Vasudevan S, Peltz S W, and Wilusz C J: Non-stop decay—a new mRNA surveillance pathway. Bioessays 2002;24:785-788.
24. Moore M J: No end to nonsense. Science 2002;298:370-371.
25. Van Dijk E, Cougot N, Meyer S, Babajko S, Wahle E, Séraphin B: Human Dcp2: a catalytically active mRNA decapping enzyme located in specific cytoplasmic structures. EMBO J 2002;21:6915-6924.
26. Ingelfinger D, Arndt-Jovin D J, Luhrmann R, and Achsel T: The human LSm1-7 proteins colocalize with the m RNA-degrading enzymes D cp1/2 and Xrnl in distinct cytoplasmic foci. RNA 2002;8:1489-1501.
27. Mazroui R, Huot M E, Tremblay S, Filion C, Labelle Y, Khandjian E W: Trapping of messenger RNA by Fragile X Mental Retardation protein into cytoplasmic granules induces translation repression. Hum Mol Genet 2002;11: 3007-3017.
28. Eystathioy, et al, Hybridoma Hybridomics 22:79-86 (2003).
29. Estathioy, et al, J. Mol Med 81:811-818 (2003).
30. Fritzler, et al., Clin Invest Med 20:50-66 (1997).

TABLE 1

SUMMARY OF FEATURES AND REACTIVITY OF FOUR MURINE MABS DIRECTED AGAINST GW182

| MAb | Isotype | IIF on ARM tissues | Immunoprecipitation of GW182 TnT product | Western blot recombinant GW182 | Western of blot HeLa cell extract | Laser of bead assay* MAb/control |
|---|---|---|---|---|---|---|
| 2D6 | IgM | Yes | Weak | Yes | No | 23758/40 |
| 4B6 | IgG1 | No | Yes | Yes | Yes | 23515/40 |
| 5C6 | IgG2a | No | Yes | Yes | No | 21144/40 |
| 6D7 | IgG1 | No | Yes | Yes | No | 11913/40 |
| Index human serum Polyclonal | | Yes | Yes | Yes | Yes | 7766/102 |

Abbreviations:
ARM, antigen retrieval methods; and
MAb, monoclonal antibody,
Tnt, transcription and translation of GW182
cDNA in rabbit reticulocyte lysate protocol.
*Units of fluorescence of MAb or the index human serum are expressed as units of fluorescence in the numerator compared to that produced by the control MAb golgin 97 or normal human serum (denominator).

TABLE 2

Demographic, clinical, and serological features of patients with anti-GWB antibodies (AMA anti-mitochondrial antibodies, mAb monoclonal antibody, NHS normal human serum, PBC primary biliary cirrhosis, Pt patient serum, IP immunoprecipitation, SjS Sj_gren's syndrome, SLE, systemic lupus erythematosus, SS-A/B Sj_gren's syndrome antigen A/B, TnT in vitro transcription and translation, UCTD undifferentiated connective tissue disease)

| Patient no. | Age (years) | Sex | Diagnosis | IIF co-localized with mAb 4B6 | SmB | Line assay SS-A 52 kDa | SS-A 60 kDa | SS-B | Laser bead assay GW 182 antibodies | |
|---|---|---|---|---|---|---|---|---|---|---|
| | | | | Group A | | | | | | |
| 1 | 73 | F | Ataxic sensory polyneuropathy | + | − | + | − | − | 7766[b] | + |
| 2 | 75 | F | Sensory neuropathy, arthritis, granuloma, silicon breast implants | + | − | + | − | − | 72 | − |
| 3 | 38 | F | Sensory neuropathy, granulomatous lymph nodes | + | − | + | − | − | 1209[b] | + |

TABLE 2-continued

Demographic, clinical, and serological features of patients with anti-GWB antibodies (AMA anti-mitochondrial antibodies, mAb monoclonal antibody, NHS normal human serum, PBC primary biliary cirrhosis, Pt patient serum, IP immunoprecipitation, SjS Sj_gren's syndrome, SLE, systemic lupus erythematosus, SS-A/B Sj_gren's syndrome antigen A/B, TnT in vitro transcription and translation, UCTD undifferentiated connective tissue disease)

| Patient no. | Age TnT IP (years) | Sex | Diagnosis | IIF co-localized with mAb 4B6 | SmB | Line assay SS-A 52 kDa | SS-A 60 kDa | SS-B | Laser bead assay GW 182 antibodies | |
|---|---|---|---|---|---|---|---|---|---|---|
| 4 | 46 | F | Malar rash, arthralgia | + | + | − | − | − | 189 | − |
| 5 | 64 | M | AMA negative PBC | + | − | + | − | − | 209 | − |
| 6 | 43 | F | UCTD | + | − | − | − | − | 123 | − |
| 7 | 51 | F | Lymphoma | + | − | − | − | − | 161 | − |
| 8 | 67 | F | Renal failure, hypergammaglobulinemia | + | − | − | − | − | 98 | + |
| 9 | 85 | F | Diabetes, heart block | + | − | − | − | − | 1014[b] | − |
| | | | Group B | | | | | | | |
| 10 | 77 | F | SjS, ataxia | + | − | + | − | − | 5999[b] | + |
| 11 | 54 | F | SjS, ataxia | + | − | + | − | − | 123 | − |
| 12 | 48 | F | SjS, motor neuropathy | + | − | + | − | − | 287 | − |
| | | | Group C | | | | | | | |
| 13 | 51 | F | SLE | + | − | − | − | − | 226 | − |
| 14 | 46 | F | SLE | + | − | − | − | − | 139 | − |
| 15 | 47 | F | SLE, SjS | + | − | − | + | − | 112 | − |
| 16 | 51 | F | SLE, SjS | + | + | + | + | + | 84 | − |
| 17 | 70 | F | SjS | + | − | − | − | − | 109 | − |
| 18 | 57 | F | SjS, interstitial pneumonitis | + | − | + | + | + | 116 | − |

[a]The results of the addressable laser bead immunoassay for antibodies to GW182 are expressed as median fluorescence units
[b]Sera with a positive test

I claim:

1. A monoclonal antibody that specifically binds to GW 182 protein or antigenic fragments thereof.

2. The monoclonal antibody of claim 1, wherein said antibody is 4B6.

3. The monoclonal antibody of claim 1, wherein said antibody binds to one or more of the epitopes of GW 182 protein corresponding to the epitopes show in FIG. 1.

4. The monoclonal antibody of claim 1, wherein the antibody is 2D6 and has a deposit number of 130204-13.

5. The monoclonal antibody of claim 1, wherein the antibody is 4B6 and has a deposit number of 130204-12.

6. The monoclonal antibody of claim 1, wherein the antibody is 5C6 and has a deposit number of 130204-14.

7. The monoclonal antibody of claim 1, wherein the antibody is 6D7 and has a deposit number of 130204-15.

8. A method of detecting the presence of GW 182 in serum comprising contacting serum suspected of containing GW 182 with a monoclonal antibody that specifically binds to GW 182 protein or antigenic fragments thereof, allowing the monoclonal antibody to bind GW 182 or antigenic fragments thereof, and detecting the presence of bound monoclonal antibody.

* * * * *

SEQUENCE LISTING

<160> NUMBER OF SEQ ID NOS: 72

<210> SEQ ID NO 1
<211> LENGTH: 15
<212> TYPE: PRT
<213> ORGANISM: HomoSapien

<400> SEQUENCE: 1

Glu Lys Asp Gly Leu Arg Asn Ser Thr Gly Leu Gly Ser Gln Asn
1               5                   10                  15

<210> SEQ ID NO 2
<211> LENGTH: 15
<212> TYPE: PRT
<213> ORGANISM: HomoSapien

<400> SEQUENCE: 2

Arg Asn Ser Thr Gly Leu Gly Ser Gln Asn Lys Phe Val Val Gly
1               5                   10                  15

<210> SEQ ID NO 3
<211> LENGTH: 15
<212> TYPE: PRT
<213> ORGANISM: HomoSapien

<400> SEQUENCE: 3

Gln Cys Ser Thr Ile Gly Gln Met Pro Asn Asn Gln Ser Ile Asn
1               5                   10                  15

<210> SEQ ID NO 4
<211> LENGTH: 15

```
<212> TYPE: PRT
<213> ORGANISM: HomoSapien

<400> SEQUENCE: 4

Gly Gln Met Pro Asn Asn Gln Ser Ile Asn Ser Lys Val Ser Gly
1               5                   10                  15

<210> SEQ ID NO 5
<211> LENGTH: 15
<212> TYPE: PRT
<213> ORGANISM: HomoSapien

<400> SEQUENCE: 5

Ser Glu Val Ser Gly Thr Gln Lys Val Ser Phe Ser Gly Gln Pro
1               5                   10                  15

<210> SEQ ID NO 6
<211> LENGTH: 15
<212> TYPE: PRT
<213> ORGANISM: HomoSapien

<400> SEQUENCE: 6

Thr Gln Lys Val Ser Phe Ser Gly Gln Pro Gln Asn Ile Thr Thr
1               5                   10                  15

<210> SEQ ID NO 7
<211> LENGTH: 15
<212> TYPE: PRT
<213> ORGANISM: HomoSapien

<400> SEQUENCE: 7

Gly Lys Thr Phe Thr Asn Gly Trp Lys Ser Thr Glu Glu Glu Asp
1               5                   10                  15

<210> SEQ ID NO 8
<211> LENGTH: 15
<212> TYPE: PRT
<213> ORGANISM: HomoSapien

<400> SEQUENCE: 8

Glu Lys Gly Thr Gly Glu Ser Gln Ser Arg Asp Arg Lys Ile
1               5                   10                  15

<210> SEQ ID NO 9
<211> LENGTH: 15
<212> TYPE: PRT
<213> ORGANISM: HomoSapien

<400> SEQUENCE: 9

Glu Ser Gln Ser Arg Asp Arg Arg Lys Ile Asp Gln His Thr Leu
1               5                   10                  15

<210> SEQ ID NO 10
<211> LENGTH: 15
<212> TYPE: PRT
<213> ORGANISM: HomoSapien

<400> SEQUENCE: 10

Asn Arg Thr Asp Leu Asp Pro Arg Val Leu Ser Asn Ser Gly Trp
1               5                   10                  15

<210> SEQ ID NO 11
<211> LENGTH: 15
<212> TYPE: PRT
<213> ORGANISM: HomoSapien
```

<400> SEQUENCE: 11

Asp Pro Arg Val Leu Ser Asn Ser Gly Trp Gly Gln Thr Pro Ile
1               5                   10                  15

<210> SEQ ID NO 12
<211> LENGTH: 15
<212> TYPE: PRT
<213> ORGANISM: HomoSapien

<400> SEQUENCE: 12

Gly Asn Asp Thr Ser Ser Val Ser Gly Trp Gly Asp Pro Lys Pro
1               5                   10                  15

<210> SEQ ID NO 13
<211> LENGTH: 15
<212> TYPE: PRT
<213> ORGANISM: HomoSapien

<400> SEQUENCE: 13

Ser Val Ser Gly Trp Gly Asp Pro Lys Pro Ala Leu Arg Trp Gly
1               5                   10                  15

<210> SEQ ID NO 14
<211> LENGTH: 15
<212> TYPE: PRT
<213> ORGANISM: HomoSapien

<400> SEQUENCE: 14

Asp Ser Lys Gly Ser Asn Cys Gln Gly Gly Trp Glu Asp Asp Ser
1               5                   10                  15

<210> SEQ ID NO 15
<211> LENGTH: 15
<212> TYPE: PRT
<213> ORGANISM: HomoSapien

<400> SEQUENCE: 15

Lys Asn Lys Gln Gly Trp Gly Asp Gly Gln Lys Ser Ser Gln Gly
1               5                   10                  15

<210> SEQ ID NO 16
<211> LENGTH: 15
<212> TYPE: PRT
<213> ORGANISM: HomoSapien

<400> SEQUENCE: 16

Trp Gly Asp Gly Gln Lys Ser Ser Gln Gly Trp Ser Val Ser Ala
1               5                   10                  15

<210> SEQ ID NO 17
<211> LENGTH: 15
<212> TYPE: PRT
<213> ORGANISM: HomoSapien

<400> SEQUENCE: 17

Lys Ser Ser Gln Gly Trp Ser Val Ser Ala Ser Asp Asn Trp Gly
1               5                   10                  15

<210> SEQ ID NO 18
<211> LENGTH: 15
<212> TYPE: PRT
<213> ORGANISM: HomoSapien

<400> SEQUENCE: 18

```
Ser Ser Gly Gly Ser Asp Ser Asp Arg Ser Val Ser Gly Trp Asn
1               5                   10                  15
```

<210> SEQ ID NO 19
<211> LENGTH: 15
<212> TYPE: PRT
<213> ORGANISM: HomoSapien

<400> SEQUENCE: 19

```
Asp Ser Asp Arg Ser Val Ser Gly Trp Asn Glu Leu Gly Lys Thr
1               5                   10                  15
```

<210> SEQ ID NO 20
<211> LENGTH: 15
<212> TYPE: PRT
<213> ORGANISM: HomoSapien

<400> SEQUENCE: 20

```
Val Ser Gly Trp Asn Glu Leu Gly Lys Thr Ser Ser Phe Thr Trp
1               5                   10                  15
```

<210> SEQ ID NO 21
<211> LENGTH: 15
<212> TYPE: PRT
<213> ORGANISM: HomoSapien

<400> SEQUENCE: 21

```
Gly Asn Asn Ile Asn Pro Asn Asn Ser Ser Gly Trp Asp Glu Ser
1               5                   10                  15
```

<210> SEQ ID NO 22
<211> LENGTH: 15
<212> TYPE: PRT
<213> ORGANISM: HomoSapien

<400> SEQUENCE: 22

```
Ser Lys Pro Thr Pro Ser Gln Gly Trp Gly Asp Pro Pro Lys Ser
1               5                   10                  15
```

<210> SEQ ID NO 23
<211> LENGTH: 15
<212> TYPE: PRT
<213> ORGANISM: HomoSapien

<400> SEQUENCE: 23

```
Ser Gln Gly Trp Gly Asp Pro Pro Lys Ser Asn Gln Ser Leu Gly
1               5                   10                  15
```

<210> SEQ ID NO 24
<211> LENGTH: 15
<212> TYPE: PRT
<213> ORGANISM: HomoSapien

<400> SEQUENCE: 24

```
Asp Pro Pro Lys Ser Asn Gln Ser Leu Gly Trp Gly Asp Ser Ser
1               5                   10                  15
```

<210> SEQ ID NO 25
<211> LENGTH: 15
<212> TYPE: PRT
<213> ORGANISM: HomoSapien

<400> SEQUENCE: 25

Asn Gln Ser Leu Gly Trp Gly Asp Ser Ser Lys Pro Val Ser Ser

```
1               5                  10                 15
```

```
<210> SEQ ID NO 26
<211> LENGTH: 15
<212> TYPE: PRT
<213> ORGANISM: HomoSapien

<400> SEQUENCE: 26
```

```
Trp Gly Asp Ser Ser Lys Pro Val Ser Pro Asp Trp Asn Lys
1               5                  10                 15
```

```
<210> SEQ ID NO 27
<211> LENGTH: 15
<212> TYPE: PRT
<213> ORGANISM: HomoSapien

<400> SEQUENCE: 27
```

```
Lys Pro Val Ser Ser Pro Asp Trp Asn Lys Gln Gln Asp Ile Val
1               5                  10                 15
```

```
<210> SEQ ID NO 28
<211> LENGTH: 15
<212> TYPE: PRT
<213> ORGANISM: HomoSapien

<400> SEQUENCE: 28
```

```
Pro Asp Trp Asn Lys Gln Gln Asp Ile Val Gly Ser Trp Gly Ile
1               5                  10                 15
```

```
<210> SEQ ID NO 29
<211> LENGTH: 15
<212> TYPE: PRT
<213> ORGANISM: HomoSapien

<400> SEQUENCE: 29
```

```
Ala Lys Glu Glu Glu Pro Thr Gly Trp Glu Glu Pro Ser Pro Glu
1               5                  10                 15
```

```
<210> SEQ ID NO 30
<211> LENGTH: 15
<212> TYPE: PRT
<213> ORGANISM: HomoSapien

<400> SEQUENCE: 30
```

```
Met Glu Ile Asp Asp Gly Thr Ser Ala Trp Gly Asp Pro Ser Lys
1               5                  10                 15
```

```
<210> SEQ ID NO 31
<211> LENGTH: 15
<212> TYPE: PRT
<213> ORGANISM: HomoSapien

<400> SEQUENCE: 31
```

```
Val Asn Met Trp Asn Lys Asn Val Pro Asn Gly Asn Ser Arg Ser
1               5                  10                 15
```

```
<210> SEQ ID NO 32
<211> LENGTH: 15
<212> TYPE: PRT
<213> ORGANISM: HomoSapien

<400> SEQUENCE: 32
```

```
Thr Pro Ala Ser Ala Ile Ser Asn Lys Glu Ala Ser Ser Gly Ser
1               5                  10                 15
```

-continued

```
<210> SEQ ID NO 33
<211> LENGTH: 15
<212> TYPE: PRT
<213> ORGANISM: HomoSapien

<400> SEQUENCE: 33

Ile Ser Asn Lys Glu Ala Ser Ser Gly Ser Gly Trp Gly Glu Pro
1               5                   10                  15

<210> SEQ ID NO 34
<211> LENGTH: 15
<212> TYPE: PRT
<213> ORGANISM: HomoSapien

<400> SEQUENCE: 34

Ala Ser Ser Gly Ser Gly Trp Gly Glu Pro Trp Gly Glu Pro Ser
1               5                   10                  15

<210> SEQ ID NO 35
<211> LENGTH: 15
<212> TYPE: PRT
<213> ORGANISM: HomoSapien

<400> SEQUENCE: 35

Gly Trp Gly Glu Pro Trp Gly Glu Pro Ser Thr Pro Ala Thr Thr
1               5                   10                  15

<210> SEQ ID NO 36
<211> LENGTH: 15
<212> TYPE: PRT
<213> ORGANISM: HomoSapien

<400> SEQUENCE: 36

Asp Asp Met Pro Leu Pro Gly Asn Arg Pro Thr Gly Trp Glu Glu
1               5                   10                  15

<210> SEQ ID NO 37
<211> LENGTH: 15
<212> TYPE: PRT
<213> ORGANISM: HomoSapien

<400> SEQUENCE: 37

Pro Gly Asn Arg Pro Thr Gly Trp Glu Glu Glu Glu Asp Val Glu
1               5                   10                  15

<210> SEQ ID NO 38
<211> LENGTH: 15
<212> TYPE: PRT
<213> ORGANISM: HomoSapien

<400> SEQUENCE: 38

Thr Gly Trp Glu Glu Glu Glu Asp Val Glu Ile Gly Asn Trp Asn
1               5                   10                  15

<210> SEQ ID NO 39
<211> LENGTH: 15
<212> TYPE: PRT
<213> ORGANISM: HomoSapien

<400> SEQUENCE: 39

Ser Ser Lys Gly Leu Ser Gly Lys Lys Arg Arg Glu Arg Gly
1               5                   10                  15

<210> SEQ ID NO 40
```

```
<211> LENGTH: 15
<212> TYPE: PRT
<213> ORGANISM: HomoSapien

<400> SEQUENCE: 40

Arg Arg Glu Arg Gly Met Met Lys Gly Gly Asn Lys Gln Glu Glu
1               5                   10                  15

<210> SEQ ID NO 41
<211> LENGTH: 15
<212> TYPE: PRT
<213> ORGANISM: HomoSapien

<400> SEQUENCE: 41

Phe Val Lys Gln Phe Ser Asn Ile Ser Phe Ser Arg Asp Ser Pro
1               5                   10                  15

<210> SEQ ID NO 42
<211> LENGTH: 15
<212> TYPE: PRT
<213> ORGANISM: HomoSapien

<400> SEQUENCE: 42

Ser Asn Ile Ser Phe Ser Arg Asp Ser Pro Glu Glu Asn Val Gln
1               5                   10                  15

<210> SEQ ID NO 43
<211> LENGTH: 15
<212> TYPE: PRT
<213> ORGANISM: HomoSapien

<400> SEQUENCE: 43

Met Glu Ile Asp Lys His Ser Leu Asn Ile Gly Asp Tyr Asn Arg
1               5                   10                  15

<210> SEQ ID NO 44
<211> LENGTH: 15
<212> TYPE: PRT
<213> ORGANISM: HomoSapien

<400> SEQUENCE: 44

His Ser Leu Asn Ile Gly Asp Tyr Asn Arg Thr Val Gly Lys Gly
1               5                   10                  15

<210> SEQ ID NO 45
<211> LENGTH: 15
<212> TYPE: PRT
<213> ORGANISM: HomoSapien

<400> SEQUENCE: 45

Phe Gly Tyr Asn Arg Thr Val Gly Lys Gly Pro Gly Ser Arg Pro
1               5                   10                  15

<210> SEQ ID NO 46
<211> LENGTH: 15
<212> TYPE: PRT
<213> ORGANISM: HomoSapien

<400> SEQUENCE: 46

Thr Val Gly Lys Gly Pro Gly Ser Arg Pro Gln Ile Ser Lys Glu
1               5                   10                  15

<210> SEQ ID NO 47
<211> LENGTH: 15
<212> TYPE: PRT
```

```
<213> ORGANISM: HomoSapien

<400> SEQUENCE: 47

Pro Gly Ser Arg Pro Gln Ile Ser Lys Glu Ser Ser Met Glu Arg
1               5                   10                  15

<210> SEQ ID NO 48
<211> LENGTH: 15
<212> TYPE: PRT
<213> ORGANISM: HomoSapien

<400> SEQUENCE: 48

Gln Ile Ser Lys Glu Ser Ser Met Glu Arg Asn Pro Tyr Phe Asp
1               5                   10                  15

<210> SEQ ID NO 49
<211> LENGTH: 15
<212> TYPE: PRT
<213> ORGANISM: HomoSapien

<400> SEQUENCE: 49

Pro Leu Ser Ser Ser Gln Pro Asn Leu Arg Ala Gln Val Pro Pro
1               5                   10                  15

<210> SEQ ID NO 50
<211> LENGTH: 15
<212> TYPE: PRT
<213> ORGANISM: HomoSapien

<400> SEQUENCE: 50

Leu Leu Lys Tyr Ala Pro Asn Asn Gly Gly Leu Asn Pro Leu Phe
1               5                   10                  15

<210> SEQ ID NO 51
<211> LENGTH: 15
<212> TYPE: PRT
<213> ORGANISM: HomoSapien

<400> SEQUENCE: 51

Pro Asn Asn Gly Gly Leu Asn Pro Leu Phe Gly Pro Gln Gln Val
1               5                   10                  15

<210> SEQ ID NO 52
<211> LENGTH: 15
<212> TYPE: PRT
<213> ORGANISM: HomoSapien

<400> SEQUENCE: 52

Leu Asn Pro Leu Phe Gly Pro Gln Gln Val Ala Met Leu Asn Gln
1               5                   10                  15

<210> SEQ ID NO 53
<211> LENGTH: 15
<212> TYPE: PRT
<213> ORGANISM: HomoSapien

<400> SEQUENCE: 53

Ser Gln Leu Gln Arg Leu Leu Ala Gln Gln Arg Ala Gln Ser
1               5                   10                  15

<210> SEQ ID NO 54
<211> LENGTH: 15
<212> TYPE: PRT
<213> ORGANISM: HomoSapien
```

```
<400> SEQUENCE: 54

Leu Leu Ala Gln Gln Gln Arg Ala Gln Ser Gln Arg Ser Val Pro
1               5                   10                  15

<210> SEQ ID NO 55
<211> LENGTH: 15
<212> TYPE: PRT
<213> ORGANISM: HomoSapien

<400> SEQUENCE: 55

Gln Arg Ala Gln Ser Gln Arg Ser Val Pro Ser Gly Asn Arg Pro
1               5                   10                  15

<210> SEQ ID NO 56
<211> LENGTH: 15
<212> TYPE: PRT
<213> ORGANISM: HomoSapien

<400> SEQUENCE: 56

Gly Arg Pro Leu Ser Val Gln Gln Gln Met Met Gln Gln Ser Arg
1               5                   10                  15

<210> SEQ ID NO 57
<211> LENGTH: 15
<212> TYPE: PRT
<213> ORGANISM: HomoSapien

<400> SEQUENCE: 57

Ser Pro Asn Gly Ser Ser Ser Val Asn Trp Pro Pro Glu Phe Arg
1               5                   10                  15

<210> SEQ ID NO 58
<211> LENGTH: 15
<212> TYPE: PRT
<213> ORGANISM: HomoSapien

<400> SEQUENCE: 58

Ser Ser Val Asn Trp Pro Pro Glu Phe Arg Pro Gly Glu Pro Trp
1               5                   10                  15

<210> SEQ ID NO 59
<211> LENGTH: 15
<212> TYPE: PRT
<213> ORGANISM: HomoSapien

<400> SEQUENCE: 59

Lys Gly Tyr Pro Asn Ile Asp Pro Glu Thr Asp Pro Tyr Val Thr
1               5                   10                  15

<210> SEQ ID NO 60
<211> LENGTH: 15
<212> TYPE: PRT
<213> ORGANISM: HomoSapien

<400> SEQUENCE: 60

Lys Pro Tyr Val Thr Pro Gly Ser Val Ile Asn Asn Leu Ser Ile
1               5                   10                  15

<210> SEQ ID NO 61
<211> LENGTH: 15
<212> TYPE: PRT
<213> ORGANISM: HomoSapien

<400> SEQUENCE: 61
```

-continued

Pro Leu Ser Ser Thr Ala Gln Ser Thr Ser Ala Arg Asn Ser Asp
1               5                   10                  15

<210> SEQ ID NO 62
<211> LENGTH: 15
<212> TYPE: PRT
<213> ORGANISM: HomoSapien

<400> SEQUENCE: 62

Ala Gln Ser Thr Ser Ala Arg Asn Ser Asp Ser Lys Leu Thr Trp
1               5                   10                  15

<210> SEQ ID NO 63
<211> LENGTH: 15
<212> TYPE: PRT
<213> ORGANISM: HomoSapien

<400> SEQUENCE: 63

Gly Gln Lys Pro Pro Leu Ser Thr Trp Asp Asn Ser Pro Leu Arg
1               5                   10                  15

<210> SEQ ID NO 64
<211> LENGTH: 15
<212> TYPE: PRT
<213> ORGANISM: HomoSapien

<400> SEQUENCE: 64

Leu Ser Thr Trp Asp Asn Ser Pro Leu Arg Ile Gly Gly Gly Trp
1               5                   10                  15

<210> SEQ ID NO 65
<211> LENGTH: 15
<212> TYPE: PRT
<213> ORGANISM: HomoSapien

<400> SEQUENCE: 65

Ser Ser Trp Gly Glu Ser Ser Gly Arg Ile Thr Asn Trp Leu
1               5                   10                  15

<210> SEQ ID NO 66
<211> LENGTH: 15
<212> TYPE: PRT
<213> ORGANISM: HomoSapien

<400> SEQUENCE: 66

Thr Thr Ile Leu Ala Glu Phe Ala Ser Glu Glu Glu Ile Ser Arg
1               5                   10                  15

<210> SEQ ID NO 67
<211> LENGTH: 15
<212> TYPE: PRT
<213> ORGANISM: HomoSapien

<400> SEQUENCE: 67

Glu Phe Ala Ser Glu Glu Glu Ile Ser Arg Phe Phe Ala Gln Ser
1               5                   10                  15

<210> SEQ ID NO 68
<211> LENGTH: 15
<212> TYPE: PRT
<213> ORGANISM: HomoSapien

<400> SEQUENCE: 68

Gln Ser Leu Thr Pro Ser Pro Gly Trp Gln Ser Leu Gly Ser Ser
1               5                   10                  15

```
<210> SEQ ID NO 69
<211> LENGTH: 15
<212> TYPE: PRT
<213> ORGANISM: HomoSapien

<400> SEQUENCE: 69

Ser Pro Gly Trp Gln Ser Leu Gly Ser Ser Gln Ser Arg Leu Gly
1               5                   10                  15

<210> SEQ ID NO 70
<211> LENGTH: 15
<212> TYPE: PRT
<213> ORGANISM: HomoSapien

<400> SEQUENCE: 70

Trp Gly Pro Pro Ser Ser Ser Asp Pro Arg Gly Ile Ser Ser Pro
1               5                   10                  15

<210> SEQ ID NO 71
<211> LENGTH: 14
<212> TYPE: PRT
<213> ORGANISM: HomoSapien

<400> SEQUENCE: 71

Ser Pro Ile Asn Ala Phe Leu Ser Val Asp His Leu Gly Gly
1               5                   10

<210> SEQ ID NO 72
<211> LENGTH: 15
<212> TYPE: PRT
<213> ORGANISM: HomoSapien

<400> SEQUENCE: 72

Ala Phe Leu Ser Val Asp His Leu Gly Gly Gly Gly Glu Ser Met
1               5                   10                  15
```